US00PP18881P2

(12) United States Plant Patent
Egger

(10) Patent No.: US PP18,881 P2
(45) Date of Patent: Jun. 3, 2008

(54) ***HEUCHERA* PLANT NAMED 'PARIS '**

(50) Latin Name: ***Heuchera* hybrid**
Varietal Denomination: Paris

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 45 days.

(21) Appl. No.: 11/638,009

(22) Filed: Dec. 12, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Annette H Para
(74) *Attorney, Agent, or Firm*—Klarquist Sparkman, LLP

(57) ABSTRACT

A new and distinct hybrid of *Heuchera* plant characterized by medium large, well-veiled, green leaves, numerous deep pink flowers, an extended bloom period, a mounding habit and excellent vigor.

1 Drawing Sheet

Botanical denomination: *Heuchera* hybrid.
Variety designation: 'Paris'.

BACKGROUND OF THE INVENTION

The present invention relates to a new and distinct cultivar of *Heuchera* and given the cultivar name of 'Paris'. *Heuchera* is in the family Saxifragaceae. *Heuchera* 'Paris' originated from a cross between *Heuchera* 'Hollywood' (U.S. Plant Pat. No. 17,129), as the seed parent, and *Heuchera* 268-2 (an unpatented, proprietary plant), as the pollen parent. Given its ornamental foliage and flower form, it is probable that *Heuchera sanguinea, H. micrantha, H. americana,* and *H. cylindrica* are in its parentage.

This new *Heuchera* is distinguished by:

1. medium large, round, well-veiled green leaves;
2. numerous deep pink flowers that fade to darker deep pink with age, giving a multi-color flower look as it matures;
3. very long bloom time;
4. mounding habit;
5. excellent vigor.

This new cultivar has been reproduced only by asexual propagation (cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

The drawing shows a two-year-old plant of *Heuchera* 'Paris' growing in the ground in the shade garden in September in Canby, Oreg.

DETAILED PLANT DESCRIPTION

The following is a detailed description of the new *Heuchera* cultivar based on observations taken in May of a two-year-old specimen grown a two gallon container in an open air shade house with 50% shade cover and added irrigation in the summer months in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Basal rosette, herbaceous perennial.
*Hardiness.*—USDA Zone 4 to 9.
*Size.*—17 cm tall from the ground to the top of the foliage and 40 cm wide.
*Habit.*—Mounding.
*Vigor.*—Excellent.
*Roots.*—Fibrous, freely branching, fine, and white in color. Roots develop easily from cuttings.

Leaf:

*Type.*—Simple.
*Arrangement.*—Rosette.
*Shape.*—Broadly ovate.
*Lobing/division.*—5 main lobes, shallow and rounded, each notched 1 to 2 times.
*Venation.*—Palmate.
*Margins.*—Broadly crenate, undulate, glandular.
*Apex.*—Mucronulate.
*Base.*—Cordate, lobes usually overlapping at the base.
*Blade size.*—8 to 11 cm long and 7 to 9.8 cm wide.
*Surface texture.*—Top surface is glabrous; bottom has very short glands along main veins.
*Petiole description.*—9 to 12 cm long and 2 mm wide with the surface having very short glandular hairs, color is Green 148A.
*Leaf color.*—Topside — Yellow Green 147A on margins and veins with an overlay of Greyed Green 198D on the rest of the leaf. On the new leave in the spring the area right next to the leaf veins is Brown 200A. Bottom side — Yellow Green 147B.

Inflorescence:

*Type.*—Thyrse, in an open wand shape.

*Number of flowers.*—About 150 per thyrse.

*Number of thyrse in spring.*—20 in the first flush, repeat blooms.

*Peduncle.*—With 0 to 1 cauline leaf, 50 cm tall and 3 mm wide at the base, Brown 200A, with glandular hairs.

*Pedicel.*—Variable in length, Greyed Purple 187A, with glandular hairs.

*Bloom period.*—May until frost in Canby, Oreg.

Flower bud:

*Size.*—3.5 mm wide and 7 mm long.

*Description.*—Glandular, ovoid, down facing.

*Color.*—Red Purple 63B with darker tips, Red Purple 63A.

Flower:

*Type.*—Perfect, zygomorphic.

*Shape.*—Campanulate.

*Size.*—7 mm long and 12 mm wide.

*Corolla.*—5 petals, 3 mm long and 1.5 mm wide, obovate with a clawed base, tip acute, margin entire to two notched, both sides with glandular hairs, reflexed, Red Purple 63C on both sides.

*Calyx.*—Campanulate, 7 mm long and 12 mm wide, 5 lobes, spreading open, divided ½ way to the base, glandular on both sides, tips acute, margin entire.

*Calyx and overall flower color.*—Inside: Red Purple 63C on the tube to Red Purple 63B on lobe bases to Red Purple 59A on lobe tips. Outside: Red Purple 59A on lobe tips and tube base, Red Purple 63B to 63C on lobes. Past maturity: Red Purple 60A.

*Stamen.*—5 in number, filaments 1 mm long, White 155D, anthers sterile, no pollen produced, oval and about 0.5 mm long, Red Purple 59A.

*Pistil.*—5 mm long, stigma and style are White 155B, stigma is 2 parted, ovary is Yellow Green 145C.

*Fragrance.*—None.

*Lastingness.*—Each thyrse blooms for about 3 weeks on the plant.

Fruit:

*Type.*—Two-beaked ovoid capsule.

*Color.*—Brown 200D.

Seed:

*Shape.*—Linear.

*Size.*—2 mm. long.

*Color.*—Black 202A.

Pest and disease tolerance: Excellent disease resistance to powdery mildew, the common problem of *Heuchera.* Susceptible to *Heuchera* rust and root weevils.

COMPARISON TO SIMILAR *HEUCHERA*

Compared to the seed parent, *Heuchera* 'Hollywood' (U.S. Plant Pat. No. 17,129), the new variety has green leaves rather than brown and a strong white veil rather than a slight veil. The flowers of the new variety are of a brighter pink color and are much more floriferous.

Compared to the pollen parent, *Heuchera* 268-2, the new variety has green leaves rather than brown and a strong white veil rather than a slight veil. The flowers of the new variety are of a brighter pink color and the inflorescences are more wand shaped.

Compared to *Heuchera* 'Strawberry Candy' (U.S. Plant Pat. No. 12,195), this new variety is much larger overall and has a much longer bloom time. It has much larger leaves, and more inflorescences and more flowers per inflorescence. The inflorescence on the new variety is longer and wider and more branched.

Compared to *Heuchera* 'Peppermint Spice' (U.S. Plant patent application Ser. No. 11/385,345), the new variety has shorter flowering stems, longer bloom time, and no dark coloration around the veins.

I claim:

1. A new and distinct hybrid of *Heuchera* plant as herein illustrated and described.

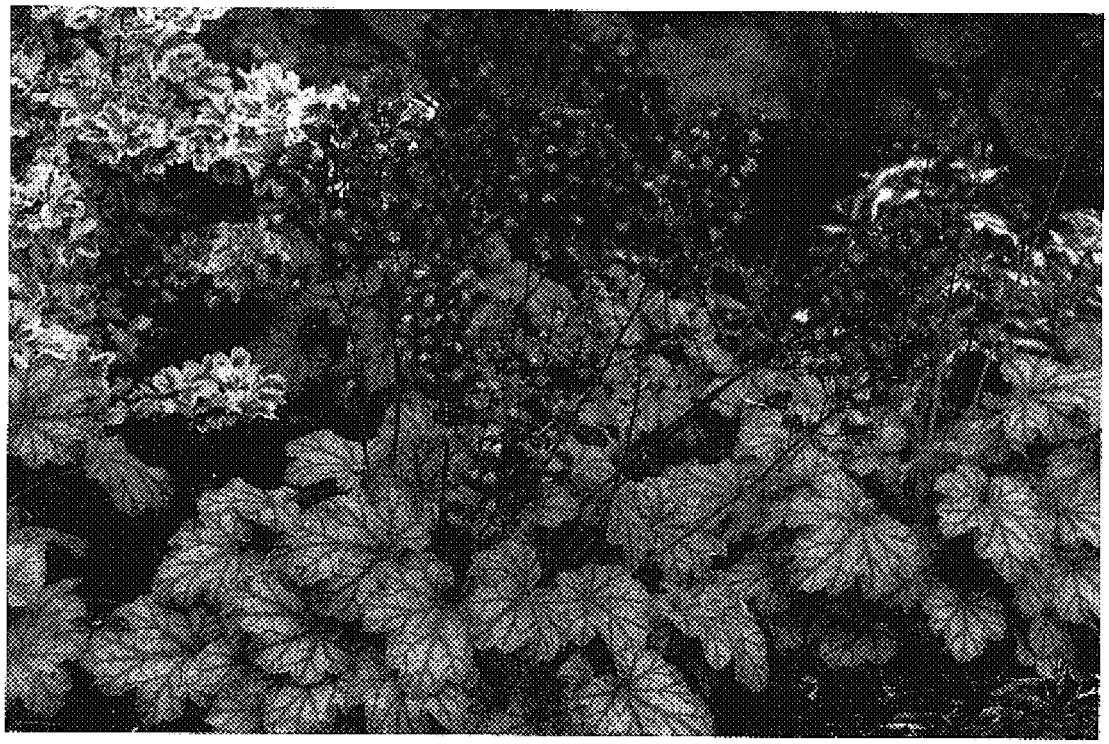

* * * * *